(12) United States Patent
Kim (10) Patent No.: US 7,375,360 B2
(45) Date of Patent: May 20, 2008

(54) LIGHT DEVICE OF ARRANGING THIN FILM INSPECTION SENSOR ARRAY, AND METHOD AND APPARATUS FOR ARRANGING SENSOR ARRAY USING THE SAME

(75) Inventor: Kyung Gu Kim, Suwon-si (KR)

(73) Assignee: LG Electronics Inc., Seoul (KR)

( * ) Notice: Subject to any disclaimer, the term of this patent is extended or adjusted under 35 U.S.C. 154(b) by 52 days.

(21) Appl. No.: 11/327,656

(22) Filed: Jan. 9, 2006

(65) Prior Publication Data

US 2006/0151725 A1    Jul. 13, 2006

(30) Foreign Application Priority Data

Jan. 10, 2005   (KR) .................... 10-2005-0002193

(51) Int. Cl.
*G01B 9/00*  (2006.01)
*G01N 21/86* (2006.01)

(52) U.S. Cl. .................. 250/559.05; 250/559.08; 250/559.44; 356/504

(58) Field of Classification Search ........... 250/559.01, 250/559.04–559.08, 559.4, 559.44; 356/485, 356/789, 492, 495, 503, 504, 511, 512, 517, 356/630, 632, 489, 450; 362/227, 341
See application file for complete search history.

(56) References Cited

U.S. PATENT DOCUMENTS 4,743,768 A * 5/1988 Watanabe .................. 250/556
6,940,604 B2 * 9/2005 Jung et al. .................. 356/503

* cited by examiner

*Primary Examiner*—John R. Lee
(74) *Attorney, Agent, or Firm*—Ked & Associates, LLP (57) ABSTRACT

There is disclosed a light device for arranging a thin film pattern sensor array where a sensor array used for inspecting a thin film pattern is made to be arranged without a separate correction pattern film in accordance with an inspection subject.

In the light device for arranging the thin film pattern sensor array, a shutter controls a width of a light beam which progresses from a light emitting element array to a sensor array. A correction pattern sled is installed in any one of a fixed location of an upper part of the shutter and a surface of the shutter to be transferable.

9 Claims, 8 Drawing Sheets

Prior Art

FIG. 4A

Prior Art

FIG. 4B

Prior Art

LIGHT DEVICE OF ARRANGING THIN FILM INSPECTION SENSOR ARRAY, AND METHOD AND APPARATUS FOR ARRANGING SENSOR ARRAY USING THE SAME

This application claims the benefit of the Korean Patent Application No. 10-2005-0002193 filed on Jan. 10, 2005, which is hereby incorporated by reference.

BACKGROUND OF THE INVENTION

1. Field of the Invention

The present invention relates to an apparatus for inspecting a thin film pattern formed on a substrate, and more particularly to a light device that is used for arranging a sensor array which is for continuously taking photographs of a thin film pattern for each line.

2. Description of the Related Art

Thin films are formed in a shape of being designed in multi-layers on a bared substrate, a wafer or a glass substrate to realize a printed circuit board, a semiconductor integrated circuit and a pixel driving circuit which drives pixel cells of a display device such as a liquid crystal display panel and a plasma display panel. In the thin film pattern, a minute defect or spot of a few micrometers µm or less can be generated in a process that the thin film formed on a substrate is patterned by a chemical etching process or a patterning process using laser beam.

The defect on the thin film pattern such as the minute defect or spot is detected by a process of photographing the surface of the substrate to make out the state of the photographed thin film pattern. An inspection apparatus used for detecting the defect on the thin film pattern includes a sensor array which photographs the substrate surface for each line so as to shorten the inspection time. The sensor array includes charge coupled devices (hereinafter, referred to as "CCD") and lenses for controlling the focus condition of each CCD. In order for the thin film pattern inspection apparatus inclusive of the sensor array to correctly detect the minute defect on the thin film pattern, an optimal focus condition of the sensor array is set in accordance with an inspection resolution as well as a coordinate system of an image generated by the sensor array and a coordinate system of a real inspection subject are to be mapped to be identical, and further the sensor array should be arranged so that an incident light to the sensor array is made to be uniform.

Figure 1:
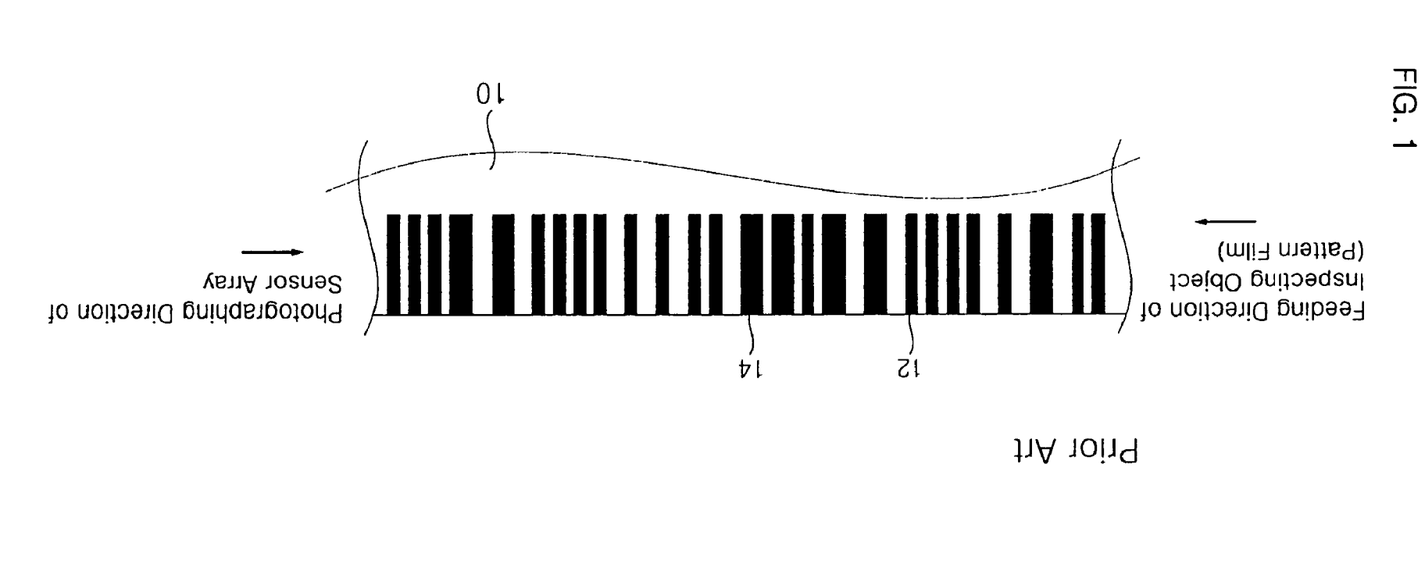
FIG. 1 is a sensor array arrangement pattern film used in a prior printed circuit board inspection device.

As a method for arranging the thin film pattern sensor array in an optimal condition, the printed circuit board inspection apparatus uses a pattern film 10 where a first black bar 12 and a second black bar 14 are printed to be mixed in a parallel direction, as shown in FIG. 1. The first black bar 12 represents a logic value '2' on its surface and the second black bar 14 represents a logic value '5'. The method controls a location and posture of each of the CCD and lens included in the sensor array in accordance with a surface condition of the pattern film 10 which is photographed by the sensor array while the pattern film 10 is fed to a reverse direction to a photographing direction of the sensor array for inspecting the printed circuit board. In this method, because a coordinate values "Rθ Φ" shown in relation to the focus of the CCD for each pixel and a start position of an image cannot be obtained, there is required an arrangement process for a separate minute adjustment.

Figure 2:
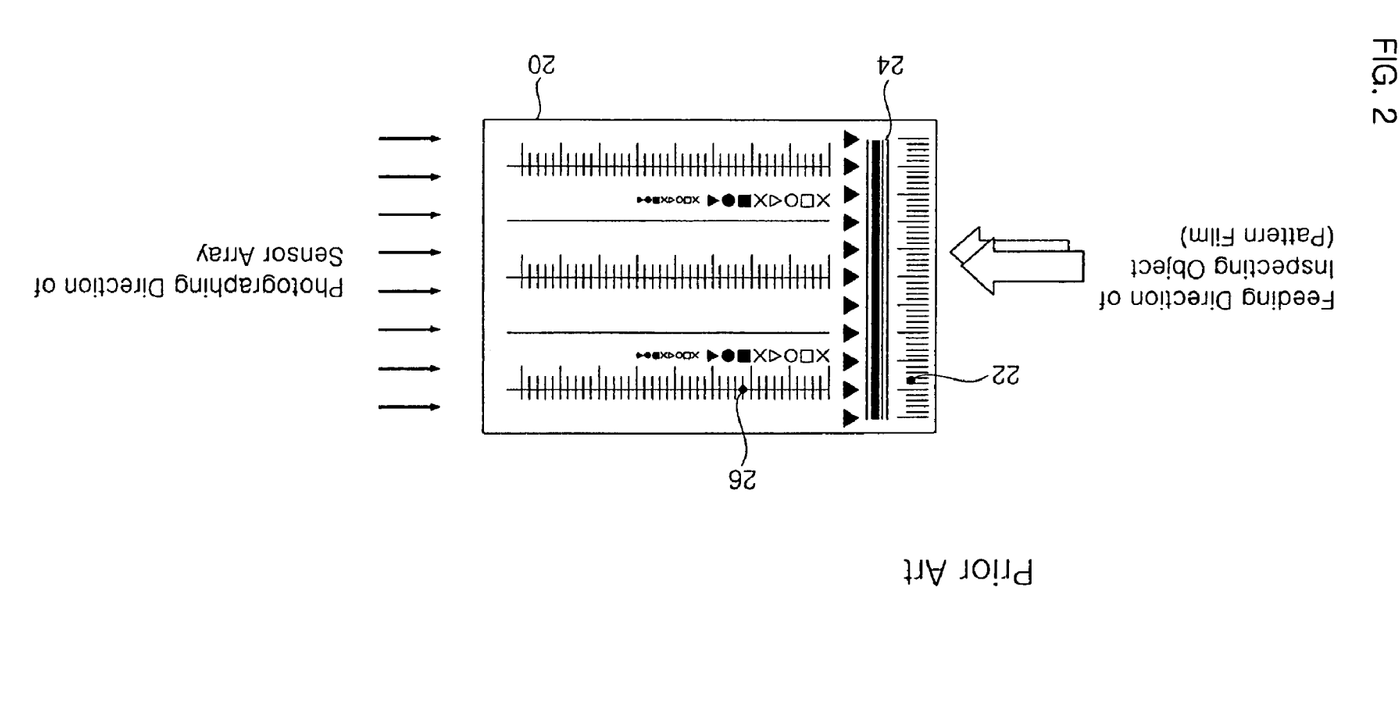
FIG. 2 is a sensor array arrangement correction pattern film used in a prior display device inspection device.

Differently from the arrangement method of the sensor array for inspecting the printed circuit board, as a method of making it possible to minutely arrange the sensor array on the basis of the focus of the CCD for each pixel and the start position of the image, there is an arrangement method of the sensor array for inspecting the display device which uses a correction pattern film 20 shown in FIG. 2. The correction pattern film 20 includes a resolution measuring pattern 22 formed to have scales of a fixed width in a fixed gap at a left edge of its own surface; and a left-right rotation correction pattern 24 formed to have thin and thick bars at the right side of the resolution measuring pattern 22. Further, patterns 26 for another inspection purpose are formed in the remaining area of the right side of the left-right rotation correction pattern 24 on the correction pattern film 20. The correction pattern film 20 as shown in FIG. 2, is fed to the reverse direction to the photographing direction of the sensor array on a light irradiating plane of the arrangement apparatus of the sensor array for inspecting the display device, thus the posture and position of each CCD and the position of each lens which are included in the sensor array can be controlled in accordance with the state of the correction pattern film 20 which is photographed by the sensor array.

Figure 3:
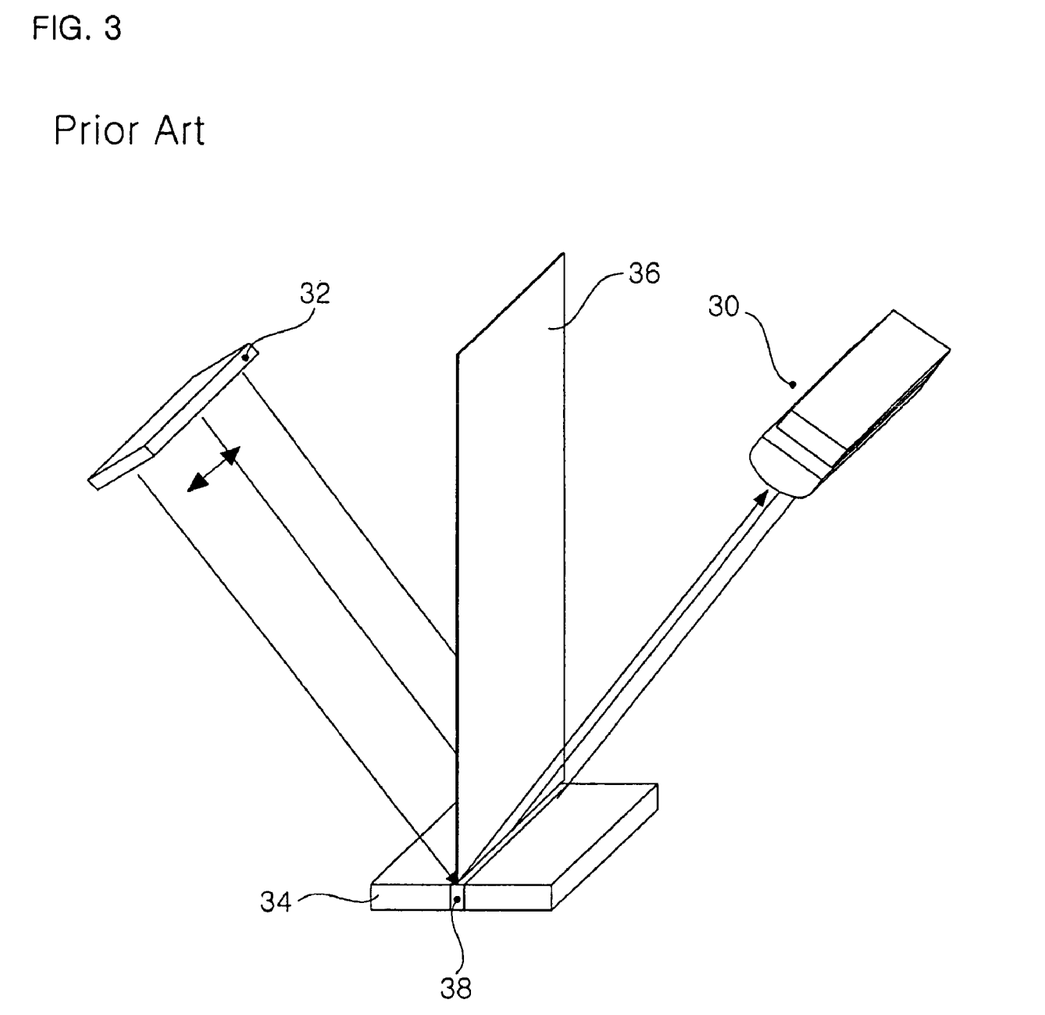
FIG. 3 is a schematic diagram illustrating a prior thin film inspection sensor array arrangement apparatus for arranging a sensor array in a display device inspection equipment.

In addition, the arrangement apparatus of the sensor array for inspecting the display device using the correction pattern film 20 of FIG. 2 includes a sensor array 30 and an light source 32 which are located to be symmetric in the right side and the left side of an irradiation datum plane 36, as shown in FIG. 3. The irradiation datum plane 36 is located in a correction target area 38 on a light irradiation plane 34 to be perpendicular to the light irradiation plane 34. The light irradiation plane 34 guides the thin film substrate of the display device when inspecting the thin film pattern of the display device, and it guides the correction pattern film 20 of FIG. 2 which is fed from the light source 32 to the sensor array 30 when arranging the sensor array.

When arranging the sensor array 30, the correction pattern film 20 of FIG. 2 is fed to the reverse direction to the photographing direction of the sensor array 30 on the light irradiation plane 34 of the arrangement apparatus of the sensor array for inspecting the display device, thus the posture and position of each CCD and the position of each lens which are included in the sensor array 30 can be controlled in accordance with the state of the correction pattern film which is photographed by the sensor array 30. The resolution measuring pattern 22 allows an adjuster (or an adjustment processor) to confirm the dimension of the surface of the pattern correction film 20 which is photographed by each CCD of the sensor array 30, thereby enabling to control the resolution. The left-right rotation correction pattern 24 allows an adjuster (or an adjustment processor) to confirm a point which is first photographed by each CCD of the sensor array 30, thereby enabling to correct a relative location of the sensor array 30 to the correction pattern film 20 and to correct a location of each CCD in an X-axis direction and a rotation amount Rθ Φ thereof for the X-axis within the sensor array. Herein, values in an X axis and an Y axis determine a start position of an image to be obtain from the subject, and a value in a Z-axis determines the focus of the image. The values are the measured amounts which uniformly appear over all the area of the sensor array, thus the location and posture of the sensor array is adjusted on the basis of the subject to adjust the values.

Figure 4A:
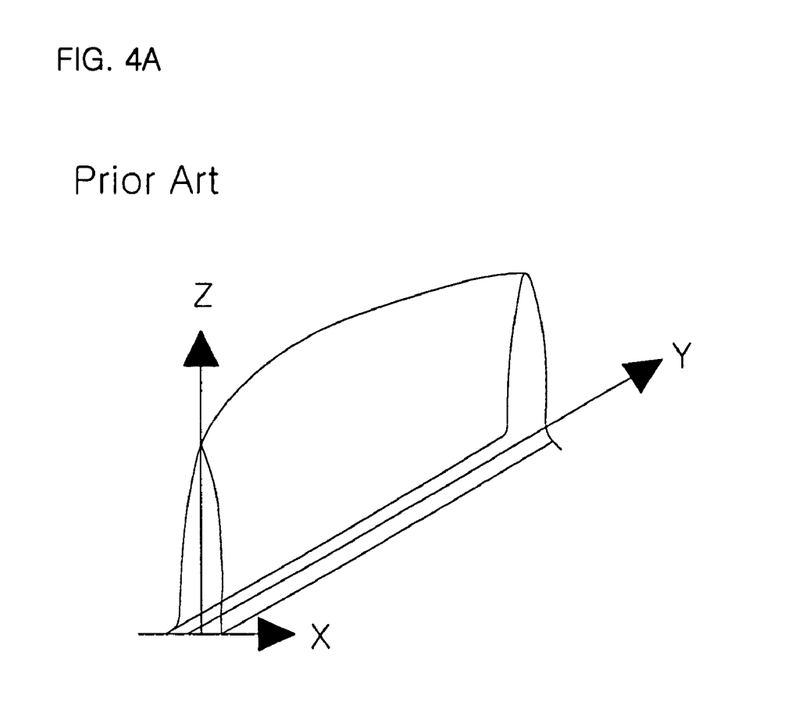
FIG. 4A is a diagram for explaining a irradiated light distribution of an light device.
Figure 4B:
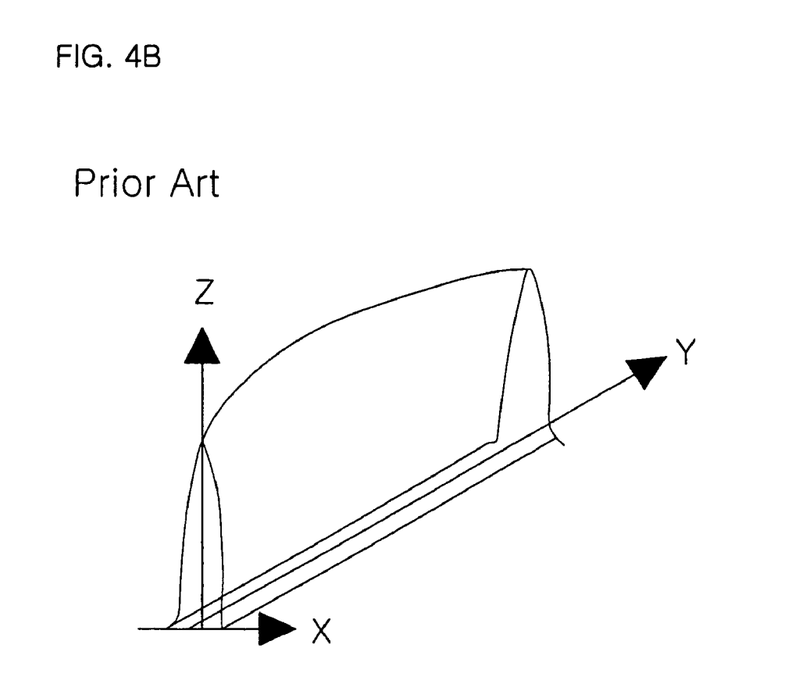
FIG. 4B is a diagram for explaining a distribution of lights which are irradiated to a correction target line.

In this way, the prior method and apparatus for arranging the sensor array for inspecting the thin film pattern require a correction pattern film 20 which is separately made in accordance with the inspection subject and the resolution required by the inspection subject. For an optimal arrangement of the sensor array 30, a distribution of a light irradiated from the light source 32 should be evenly kept in a section from one end of the light source 32 to the other end thereof. However, the light irradiated in the section from the one end of the light source 32 to the other end in the prior arrangement apparatus of the sensor array for inspecting the thin film pattern is not uniformly distributed, as shown in FIG. 4A. In addition to this, the distribution of the light irradiated from the light source 32 to the correction target area 38 on the light irradiation plane 34, as shown in FIG. 4B, is hard to be evenly kept over all the section from one end of the correction target area 38 to the other end thereof. The uniformity of the light distribution and the correction pattern film 20 becomes worse as the thin film pattern is made in a large size because the liquid crystal display panel and the plasma panel are large-sized.

SUMMARY OF THE INVENTION

Accordingly, it is an object of the present invention to provide a light device for arranging a sensor array where the sensor array used for inspecting a thin film pattern is made to be arranged without a separate correction pattern film in accordance with an inspection subject.

It is another object of the present invention to provide a method and apparatus for arranging a sensor array for a thin film pattern which can arrange the sensor array without a separate correction pattern film in accordance with an inspection subject.

An embodiment of an aspect of the present invention relates to a light device which is used for arranging a thin film pattern inspection sensor array. An embodiment of another aspect of the present invention relates to a method and apparatus used for arranging a thin film pattern sensor array.

In order to achieve these and other objects of the invention, a light device for arranging a thin film pattern sensor array according to an aspect of the present invention includes a light emitting element array for irradiating light; a shutter for controlling a width of a light beam which progresses from the light emitting element array to the sensor array; and a correction pattern sled installed to be movable in any one of a fixed location of an upper part of the shutter and a surface of the shutter.

The light emitting element array includes a chip type LED array where chip type LEDs are arranged in series. The chip type LED can individually adjust the amount of an irradiated light.

The light device further includes a focusing member for progressing a light irradiated from the light emitting element array to the shutter.

The focusing member includes any one of an acryl and an optical fiber having a half-circled cross section so as to cover the light emitting element array.

The light device further includes a diffusion plate for making a distribution of a light uniform. The lights from the light emitting element array progress to the shutter in parallel.

A thin film pattern sensor array arrangement apparatus according to an embodiment of another aspect of the present invention includes a sensor array for continuously sensing a thin film pattern for each line; and a self-light device being installed in an area where the thin film pattern to be sensed by the sensor array is located and irradiating lights required for adjustment of a location and posture of the sensor array.

A method of arranging a thin film pattern sensor array according to an embodiment of still another aspect of the present invention includes the steps of mounting the self-light device in an area where a thin film pattern to be sensed by the sensor array is located; adjusting a gap of the shutter and adjusting a rotation amount of the sensor array on the basis of an output from the sensor array; and adjusting a location of the sensor array on X, Y and Z axes on the basis of the output from the sensor array while transferring the correction pattern sled.

According to the light apparatus for arranging the sensor array of the present invention configured as described above, the correction arrangement pattern film which was separately used in accordance with an inspection subject can be removed, and an irradiated light distribution is uniformly sustained in the whole section of a line light emitting area of the self-light device.

In addition to this, according to the method and apparatus for arranging the thin film pattern sensor array, the self-light device is located in a correction target area on a light irradiation plane which is an area where an inspection subject is photographed, thereby decreasing the size of the arrangement device.

The object and other objects of the present invention will be apparent from the following detailed description. However, even though the detailed description is made in a way of only explaining the preferred embodiment of the present invention or the examples of the specific number, it should be understood to the ordinary skilled person in the art that various changes or modifications thereof are possible without departing from the spirit of the invention from the detailed description.

BRIEF DESCRIPTION OF THE DRAWINGS

These and other objects of the invention will be apparent from the following detailed description of the embodiments of the present invention with reference to the accompanying drawings, in which.

DETAILED DESCRIPTION OF THE PREFERRED EMBODIMENT

Figure 5:
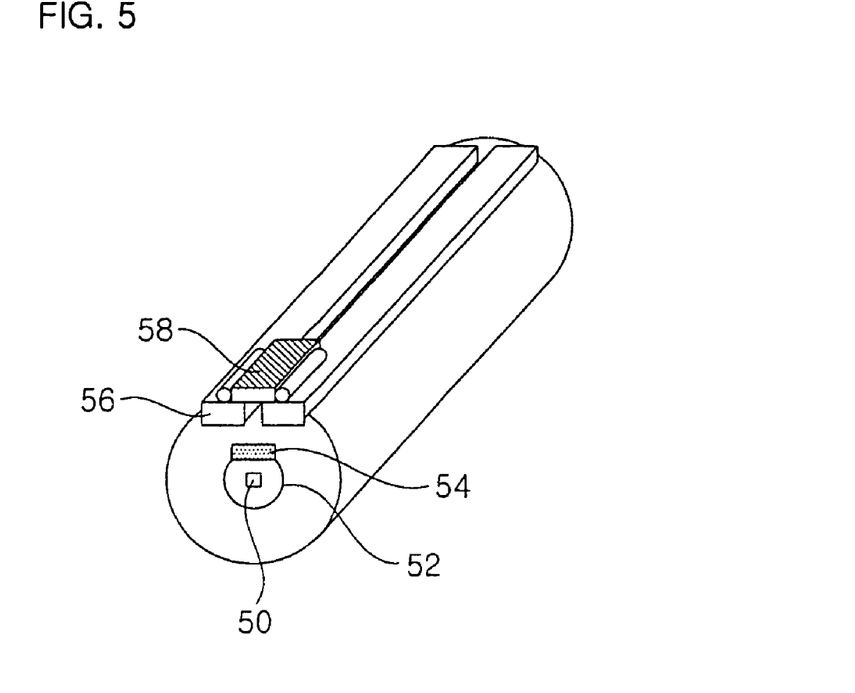
FIG. 5 is a schematic diagram illustrating a light device according to an embodiment of the present invention.

FIG. 5 is a diagram briefly illustrating a light device for arranging a thin film pattern sensor array according to an embodiment of the present invention. The light device is located at a correction target area of a prior sensor array arrangement device of FIG. 3, i.e., at an area where a sensor array photographs a thin film pattern when inspecting the thin film pattern, to directly irradiate lights to the sensor array, thereby enabling to adjust the location and posture of the sensor array.

The light device according to the embodiment of the present invention includes a chip type LED array 50 provided within a focusing member 52; a diffusion plate 54 installed in a flat plane of the focusing member 52; and a slit type shutter 56 installed to face the diffusion plate 54 with a fixed distance therebetween. The chip type LED array 50, the focusing member 52, the diffusion plate 54 and the slit type shutter 56 all have the same length as the sensor array.

Figure 6:
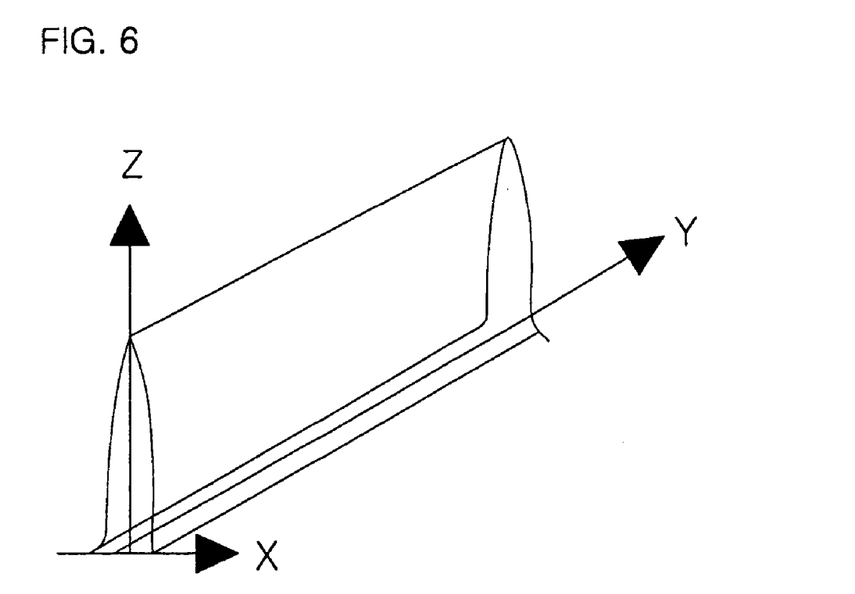
FIG. 6 is a distribution diagram of lights emitted from a light emitting plane of the light device.

The chip type LED array 50 includes a plurality of chip type LEDs which are arranged in series in the same manner as a CCD array within the sensor array. Each of the chip type LEDs within the chip type LED array 50 is electrically controlled to be able to control the amount of lights to be irradiated to the sensor array. The chip type LEDs are each controlled electrically, the distribution of the irradiated lights in a longitudinal direction of the chip type LED array 50 is uniform, as shown in FIG. 6.

The focusing member 52 makes the lights from the chip type LED array 50 progress in one direction, i.e., to the sensor array. To this end, the focusing member 52 is made of an optical fiber or an acrylic rod of which the cross section is a half circle. The acrylic rod or optical fiber reflects the lights from the chip type LED array 50 to a flat aperture plane to make the light progress only to the sensor array.

The diffusion plate 54 diffuses the lights which progresses from the chip type LED array 50 to the sensor array, so that the light passing through its own plane is uniformly distributed to be planar. The diffusion plate 54 might be installed to face the flat plane of the focusing member 52 with a distance therebetween.

The slit type shutter 56 installed to face the diffusion plate 54 with a fixed distance therebetween in an upper part of the focusing member 52 adjusts the distance of the gap formed in a longitudinal direction, thereby controls a width of a line type light beam which progresses from the diffusion plate 54 to the sensor array. The rotation for the X, Y and Z axes of each CCD's within the sensor array is minutely adjusted by the gap formed by the slit type shutter 56, and the location of the lens within the sensor array is adjusted, thereby making the posture of the sensor array corrected. The width of the gap formed by the slit type shutter 56 is adjusted in accordance with the precision of the posture required by the sensor array. Further, the slit type shutter 56 is desired to be made in a cylinder shape to encompass the focusing member 52 in order to increase the efficiency of light.

The light device further includes a correction pattern sled 58. The correction pattern sled 58 is installed in the upper part or surface of the slit type shutter 56 to be able to be transferred. The correction pattern sled 58 is also transferred in a longitudinal direction by an electrical control to make the location and posture, which are related to the resolution of each of the CCD's within the CCD array included in the sensor array, corrected sequentially and in a unit of fixed numbers from the CCD of one side end of the CCD array to the CCD of the other side end. The correction pattern sled 58 where scales of which the distance is different in accordance with the resolution are marked in divided areas is used, or it can be used in a form of being replaced with another pattern part which is printed with scales of which the distance is different in accordance with the resolution.

The slit type shutter 56 and the transferable correction pattern sled 58 remove the correction pattern film which was separately required by the related art sensor array arrangement device in accordance with the resolution and optical precision. Further, the chip type LEDs which can individually control the amount of the irradiated light are arranged in series, thus the distribution of the irradiated light becomes uniform in the whole section from one end of the linear light source to the other end, as shown in FIG. 6.

Figure 7:
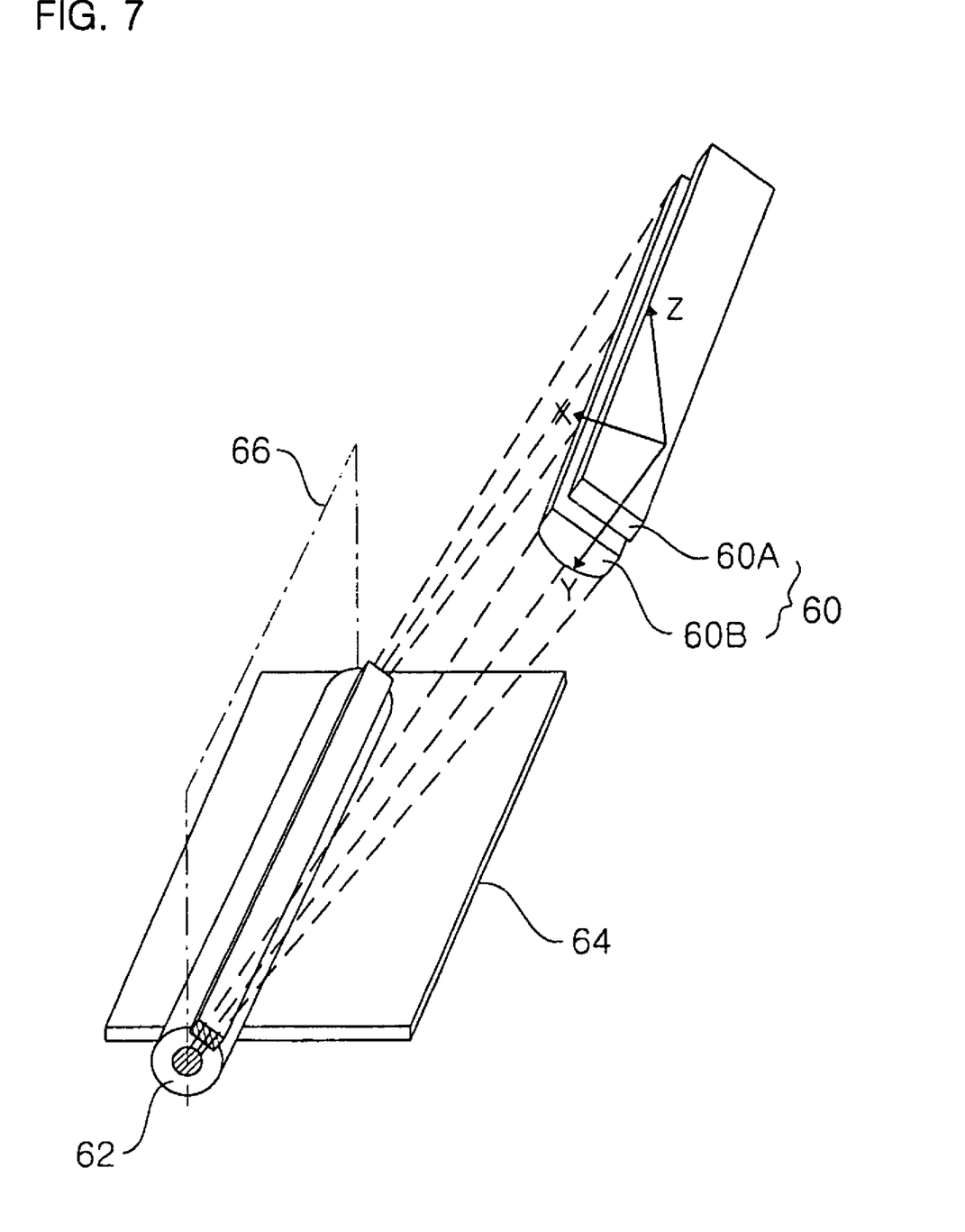
FIG. 7 is a diagram briefly illustrating an optical system of a display device inspection sensor array arrangement apparatus according to an embodiment of the present invention.

Referring to FIG. 7, the optical system of the thin film inspection sensor array arrangement apparatus according to an embodiment of the present invention includes a sensor array 60 located in an upper part of a feeding plane 64 of an inspection subject; a self-light device 62 located on the feeding plane 64 of the inspection subject or a lower part thereof. The sensor array 60 is installed in the right side of the irradiation datum plane 66 with a fixed distance therebetween so that the light from the self-light device 62 is slantingly incident. The irradiation datum plane 66 is located in the self-light device 62 to form a right angle with the feeding plane 64 of the inspection subject. The self-light device 62 is located at a correction target area in the related art sensor array arrangement device of FIG. 3, i.e., at an area where the sensor array 60 photographs the thin film pattern when inspecting the thin film pattern.

The sensor array 60 includes a CCD array 60A where a plurality of CCDs are arranged in series; and a lens 60B located at a lower part of the CCD array 60A. The CCD array 60A is long, e.g., a length of 1500 mm or more, to be suitable for continuously photographing the thin film pattern of a large screen for each line. Each of the CCDs included in the CCD array 60A is combined to minutely move to forward, backward, left and right as well as upward and downward to be able to adjust the relative location and posture for the self-light device 62.

The lens 60B is installed at the lower part of the CCD array 60A to be able to move between the CCD array 60A and the self-light source 62 so that the light from the self-light source 62 is focused to each of the CCDs of the CCD array 60A. To this end, the lens 60B is made to have the same length as the CCD array 60A.

A distance between the CCD array 60A and the lens 60B is adjusted by the movement of the lens 60B, thereby roughly controlling the focus of each of the CCDs within the CCD array 60A. Subsequently, the posture and location of each CCD for the self-light device 62 are minutely adjusted by the minute movement of forward, backward, right, left, up and down of each of the CCDs within the CCD array 60A, thus the resolution, the photographed pixel area and arrangement are adjusted when photographing the inspection subject.

The self-light device 62 is made to have the same length as the sensor array 60, i.e., as the CCD array 60A and the lens 60B, so that the light to be irradiated to the sensor array 60 is uniform when adjusting the location and posture of the sensor array 60. In addition, the self-light device 62 can adjust the photographing resolution of the sensor array 60 and the pixel area and its arrangement.

Figure 8:
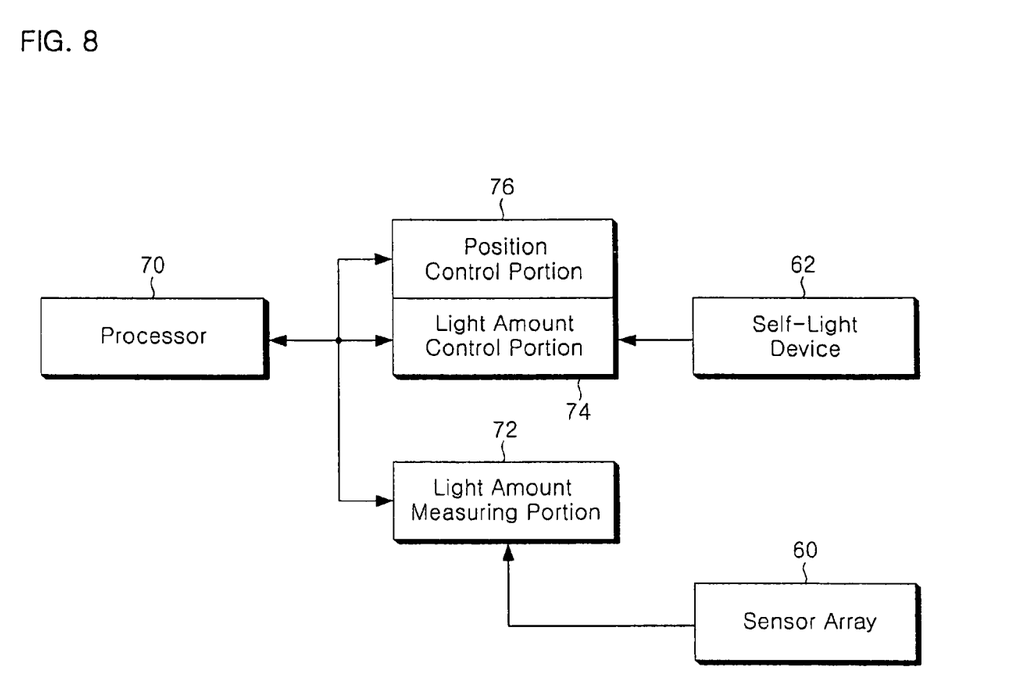
FIG. 8 is a block diagram of a drive circuit for driving a light source device shown in FIG. 7.

Referring to FIG. 8, the drive circuit for driving the optical system of the thin film pattern sensor array arrangement apparatus includes a light amount measuring portion 72, a light amount control portion 74 and a position control portion 76 which are commonly connected to a processor 70.

The light amount measuring portion 72 calculates a light amount from a light detection signal from the CCD array 60A within the sensor array 60 to supply to the processor 70. At this moment, the light amount measuring portion 72 sequentially calculates the light amount photographed by all the CCDs included in the CCD array 60A under control of the processor 70 to sequentially supply the calculated values to the processor 70 or the light amount measuring portion 72 calculates the light amount photographed by the CCDs within a designated section after being divided for each fixed section so as to supply the calculated values to the processor 70. In order to calculate the light amount for the CCD designated by the processor 70, the light amount measuring portion 72 receives a CCD address from the processor 70, wherein the CCD address indicates each of the CCDs within the CCD array 60A.

The light amount control portion 74 electrically adjusts the amount of the irradiated light of each of the chip type LEDs of the chip type LED array 50 designated by the processor 70 under control of the processor 70. To this end, the light amount control portion 74 receives a light amount control value and the LED address indicating the chip type LED within the chip type LED array 60 from the processor 70.

The position control portion 76 minutely adjusts the location of each CCD within the CCD array 60A on the X, Y and Z axes and a rotation amount on each axis under control of the processor 70, and it adjusts the location of the lens 60B. The position control portion 76 can receive only a mode address which indicates the CCD array 60A, the lens 60B and the chip type LED array 50, or it can receive a CCD address indicating each CCD within the CCD array 60A or an LED address indicating each chip type LED within the chip type LED array 50. In addition to this, the position control portion 76 receives a control value for the location of each CCD on the X, Y and Z axes and the rotation amount on each axis and a control value for the location of the lens 60B from the processor 70.

The processor 70 inputs a value for the amount of the lights which are incident to each CCD within the CCD array 60A from the light amount measuring portion 72 and adjusts the amount of the irradiated lights of each chip type LED within the chip type LED array 50 through the light amount control portion 74 on the basis of the light amount value thereof, thus the irradiated light distribution in the whole section from one end of the self-light device 62 and the other end is made to be uniform. In addition, the processor 70 inputs a value for the amount of the lights which are incident to each CCD within the CCD array 60A from the light amount measuring portion 71, thereby adjusting the location of the lens 60B, and the location of each CCD within the CCD array 60A on the X, Y and Z axes and the rotation posture on each axis through the position control portion 76 on the basis of the light amount value thereof. For such a control, the processor 70 performs the operation according to the sequence as shown in the flow chart of FIG. 9.

Figure 9:
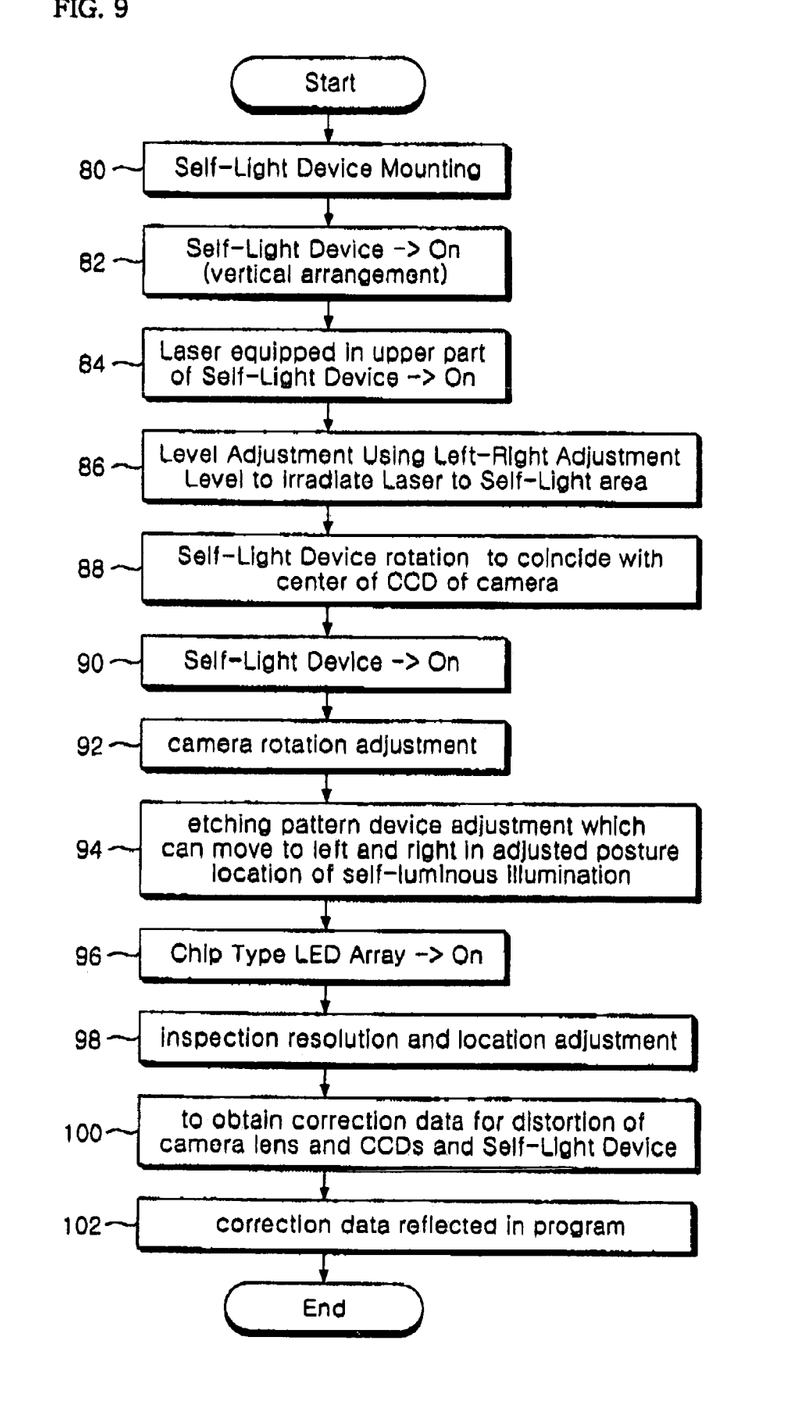
FIG. 9 is a flow chart for explaining an arrangement method of a display device inspection sensor array according to an embodiment of the present invention, step by step.

FIG. 9 is a flow chart for explaining a thin film pattern inspection sensor array arrangement method according to an embodiment of the present invention.

According to FIG. 9, the light device as shown in FIG. 5, in detail, the self-light device 62 is mounted in a location where the sensor array 60 photographs the thin film pattern by the operator, i.e., a correction target area. (step 80) The mounted self-light device 62 has its posture adjusted so that the light can be irradiated along the datum irradiation plane 66. (step 82) An arrangement operator installs a laser light source in an irradiation direction of the self-light device 62 to drive the laser light source. (step 84) Subsequently, the arrangement operator adjusts the level of the self-light device 62 by use of a left-right adjustment level until a laser beam is irradiated to a light irradiation area of the self-light device 62. (step 86) Such an adjustment and a monitoring through the sensor array are carried out together. In this way, if the laser beam is irradiated to the light irradiation area of the self-light device 62, the arrangement operator rotates the self-light device 62 so that a light irradiation direction of the self-light device 62 coincides with that of the center of the sensor array 60. (step 88)

Steps 90 to 102 after the step 88 are automatically performed by the processor 70. The processor 70 drives the chip type LED array 50 within the self-light device 62 through the light amount control portion 74 to make the light irradiated to the sensor array 60. (step 90) The processor 70 inputs the light amount photographed by the sensor array 60 from the light amount measuring portion 72 the rotation R$\theta$ $\Phi$ of the sensor array 60 through the position control portion 76 on the basis of the inputted light amount, thus the rough location of the sensor array 60 and the self-light device 62, the location of the lens 60B within the sensor array 60, and the location of each CCD within the CCD array 60A on the X, Y and Z axes and the rotation posture on each axis are adjusted. (step 92) In the adjustment step, the processor 70 displays its adjustment result value to a monitor (not shown). The value displayed in the monitor is displayed in a graph and a numeric value and is a distance value between the patterns which are printed in an equal distance. If not a level value but an inclined value is displayed on the graph, the location and posture of the sensor array 60 is adjusted by the position control portion 76 until the level value is calculated. After being adjusted in this way, a brightness value graph for the same pattern is displayed on the monitor and the brightness value graph should also have a level value which is included within a fixed range.

Subsequently, the correction pattern portion 58 is mounted in the self-light device 62 by the arrangement operator (step 94), and the processor 70 drives the chip type LED array 50 again within the self-light device 62 through the light amount control portion 74 to make the light irradiated to the sensor array 60. (step 96) As the arrangement operator transfers the correction pattern portion 58 mounted in the self-light device 62 from one end of the self-light device 62 to the other end, the processor 70 inputs the light amount photographed by the sensor array from the light amount measuring portion 72, thereby adjusting the location of the lens 60B within the sensor array 60 related to the resolution and the location of each CCD within the CCD array 60A on the X, Y and Z axes on the basis of the inputted light amount through the position control portion 76. (step 98)

Next, the process 70 calculates a correction data for distortion of each CCD within the CCD array 60A, the lens 60A within the sensor array 60 and the self-light device 62 (step 100), the calculated correction data is reflected in the pattern inspection program which is used for inspecting the thin film pattern. (step 102)

Through such an arrangement sequence, the optical system is adjusted to have a fixed resolution as well as a light irradiation from the self-light device 62 for the sensor array 60 is performed correctly. In setting the optical system, a micrometer is mounted in the adjustment part to enable a minute adjustment.

On the other hand, the slit type shutter 56 is fully opened in the first place to be controlled for the light to be irradiated to a wide surface in a low intensity, thereby setting a rough standard location between the sensor array 60 and the self-light device 62. Subsequently, the slit type shutter 56 is gradually closed to make the light irradiated to an area which becomes narrower in a gradually higher intensity, thereby increasing the extent of the arrangement of each CCD within the CCD array 60A and the lens 60B within the sensor array 60.

As described above, the thin film pattern sensor array arrangement light device according to the embodiment of the present invention can remove (or prevent) the use of the correction arrangement pattern film which should be separately used in accordance with the inspection subject when arranging the sensor array by use of the slit type shutter and the transferable correction pattern sled. In addition, the thin film pattern sensor array arrangement light device according to the embodiment of the present invention locally controls the irradiated light amount in the line light emitting area by use of the chip type LED, thereby uniformly sustaining the irradiated light distribution in the whole section of the line light emitting area of the light device.

The method and apparatus for arranging the thin film pattern sensor array according to the embodiment of the present invention can remove (or prevent) the use of the correction arrangement pattern film which should be separately used in accordance with the inspection subject when arranging the sensor array by use of the light device having the slit type shutter and the transferable correction pattern sled. In addition, the thin film pattern sensor array arrangement light device according to the embodiment of the present invention locally controls the irradiated light amount in the line light emitting area by use of the light device having the chip type LED, thereby uniformly sustaining the irradiated light distribution in the whole section of the line light emitting area of the light device. In addition, the light device is located in the correction target area on the light irradiation plane which is an area where the inspection subject is photographed, thereby decreasing the size.

Although the present invention has been explained by the embodiments shown in the drawings described above, it should be understood to the ordinary skilled person in the art that the invention is not limited to the embodiments, but rather that various changes or modifications thereof are possible without departing from the spirit of the invention. Accordingly, the scope of the invention shall be determined only by the appended claims and their equivalents.

What is claimed is:

1. A thin film pattern sensor array arrangement apparatus, comprising:
   a sensor array that continuously senses a thin film pattern comprising a plurality of lines provided in a surface of the pattern facing the sensor array; and
   a self-light device provided proximate the thin film pattern, wherein the self-light device irradiates light toward the sensor array, and wherein the sensor array receives the irradiated light and adjusts a position of components of the sensor array based on the received irradiated light.

2. The thin film pattern sensor array arrangement device according to claim 1, wherein the self-light device includes:
   a light emitting element array that irradiates light toward the sensor array;
   a shutter that controls a width of a light beam transmitted from the light emitting element array to the sensor array; and
   a correction pattern sled movably coupled to the shutter, and positioned between the light emitting element array and the sensor array.

3. The thin film pattern sensor array arrangement apparatus according to claim 2, further comprising:
   a focusing member that focuses light irradiated by the light emitting element array and directs the irradiated light to the shutter.

4. The thin film pattern sensor array arrangement apparatus according to claim 3, wherein the focusing member is an optical fiber having a semi-circular cross section so as to cover the light emitting element array.

5. The thin film pattern sensor array arrangement apparatus according to claim 3, further comprising:
   a diffusion plate that uniformly distributes light emitted by the light emitting element array as it is directed to the shutter.

6. The thin film pattern sensor array arrangement apparatus according to claim 3, wherein the light emitting element array includes:
   a chip type LED array comprising a plurality of chip type LEDs arranged in series, wherein the chip type LED individually adjusts an amount of light irradiated by each of the chip type LEDs.

7. The thin film pattern sensor array arrangement apparatus according to claim 2, further comprising:
   a diffusion plate that uniformly distributes irradiated light as it progresses from the light emitting element array to the shutter.

8. The thin film pattern sensor array arrangement apparatus according to claim 2, wherein the light emitting element array includes:
   a chip type LED array comprising a plurality of chip type LEDs arranged in series, wherein the chip type LED array individually adjusts an amount of light irradiated by each of the chip type LEDs.

9. A method of arranging a thin film pattern sensor array using a sensor array that continuously senses a thin film pattern comprising a plurality of lines, and a self-light device having a shutter that controls a width of a light beam which progresses from a light emitting element array to the sensor array and a correction pattern sled movably coupled to the shutter, the method comprising:
   mounting the self-light device proximate a thin film pattern to be sensed by the sensor array;
   adjusting a gap of the shutter and adjusting a rotation amount of the sensor array based on an output from the sensor array; and
   adjusting an orientation of at least one component of the sensor array based on the output from the sensor array as the correction pattern sled moves relative to the shutter.

* * * * *